(12) United States Patent
Feng et al.

(10) Patent No.: US 10,076,287 B2
(45) Date of Patent: Sep. 18, 2018

(54) METHOD FOR MONITORING PHYSIOLOGICAL STATUS OF VEHICLE DRIVER

(71) Applicant: AUTOMOTIVE RESEARCH & TESTING CENTER, Lugang Chen, Changhua Hsien (TW)

(72) Inventors: Yen-Cheng Feng, Changhua Hsien (TW); Jih-Tao Hsu, Changhua Hsien (TW); Hsuan-Yu Huang, Changhua Hsien (TW); Chun-Yao Shih, Changhua Hsien (TW)

(73) Assignee: AUTOMOTIVE RESEARCH & TESTING CENTER, Lugang Chen, Changhua Hsien (TW)

( * ) Notice: Subject to any disclaimer, the term of this patent is extended or adjusted under 35 U.S.C. 154(b) by 350 days.

(21) Appl. No.: 14/982,464

(22) Filed: Dec. 29, 2015

(65) Prior Publication Data
US 2017/0181713 A1    Jun. 29, 2017

(51) Int. Cl.
*A61B 5/021*    (2006.01)
*A61B 5/00*    (2006.01)
*A61B 5/18*    (2006.01)
*A61B 5/0205*    (2006.01)
*A61B 5/145*    (2006.01)
(Continued)

(52) U.S. Cl.
CPC .......... *A61B 5/7282* (2013.01); *A61B 5/0205* (2013.01); *A61B 5/18* (2013.01); *A61B 5/746* (2013.01); *A61B 5/021* (2013.01); *A61B 5/02405* (2013.01); *A61B 5/02416* (2013.01); *A61B 5/14532* (2013.01); *A61B 5/14551* (2013.01); *A61B 5/7475* (2013.01)

(58) Field of Classification Search
CPC ...... A61B 5/7282; A61B 5/02405; A61B 5/18
See application file for complete search history.

(56) References Cited

U.S. PATENT DOCUMENTS 7,463,157 B2 * 12/2008 Victor ...................... A61B 5/11
                                                                    180/272
8,676,444 B2 *  3/2014 Van Dongen ......... B60W 30/12
                                                                    180/272

(Continued)

*Primary Examiner* — Christopher D Koharski
*Assistant Examiner* — Amanda Steinberg
(74) *Attorney, Agent, or Firm* — patenttm.us

(57) ABSTRACT

A method for monitoring physiological status of a vehicle driver is performed by a monitoring device connected to a physiological sensor and comprises steps of: (a) establishing a personal physiological database comprising steps of: periodically sensing the vehicle driver via the physiological sensor to obtain the physiological signals within an initial duration; obtaining a mean value and a standard deviation based on the physiological signals; and obtaining a tolerance range based on the mean value and the standard deviation, such that the personal physiological database stores the tolerance range; (b) sensing the vehicle driver via the physiological sensor to obtain at least one instant physiological signal after the initial duration; and (c) determining whether the at least one instant physiological signal is out of the tolerance range, such that an alarm is outputted when the at least one instant physiological signal is out of the tolerance range.

11 Claims, 10 Drawing Sheets

(51) Int. Cl.
*A61B 5/1455* (2006.01)
*A61B 5/024* (2006.01)

(56) References Cited

U.S. PATENT DOCUMENTS

| | | | | |
|---|---|---|---|---|
| 8,886,365 | B2* | 11/2014 | Filev | B60Q 9/00 340/438 |
| 2007/0265540 | A1* | 11/2007 | Fuwamoto | A61B 5/04525 600/515 |
| 2009/0247848 | A1* | 10/2009 | Baker, Jr. | A61B 5/14551 600/323 |
| 2010/0217099 | A1* | 8/2010 | LeBoeuf | A61B 5/00 600/301 |
| 2013/0070043 | A1* | 3/2013 | Geva | B60K 28/066 348/14.02 |

* cited by examiner

METHOD FOR MONITORING PHYSIOLOGICAL STATUS OF VEHICLE DRIVER

BACKGROUND OF THE INVENTION

1. Field of the Invention

The present invention relates to a method for monitoring physiological status, and more particularly to a method for monitoring physiological status of a vehicle driver.

2. Description of Related Art

Human behaviors may reflect the physiological status. Abnormal physiological status would affect the human action. For example, high blood sugar may induce dehydration, rapid heartbeats, arrhythmia, or low blood pressure. A person having high blood sugar may even suffer from shock. Low blood sugar may induce palpitations, headaches, dizziness, weakness, tiredness, or rapid heartbeats. High blood oxygen saturation may induce tiredness, poor concentration, drowsiness, or rapid heartbeats. High blood pressure may induce headaches, drumming in the ears, shortness of breath, or rapid heartbeats. Low blood pressure may induce dizziness, lack of strength, or arrhythmia because the blood supplied to the brain is insufficient. A person with low blood pressure may lose the consciousness and fall down.

Hence, the physiological status of a vehicle driver is closely related to driving safety. When the action of the vehicle driver is affected by abnormal physiological status, for example, the vehicle driver may have poor concentration, drowsiness, or weakness, and the vehicle driver fails to stably drive the vehicle and increases the chance of causing a traffic accident.

SUMMARY OF THE INVENTION

An objective of the present invention is to provide a method for monitoring physiological status of a vehicle driver. When the physiological status of the vehicle driver is abnormal, an alarm would be outputted to warn the vehicle driver.

The method of the present invention is performed by a monitoring device electrically connected to a physiological sensor. The physiological sensor is adapted to sense a vehicle driver to obtain physiological signals of the vehicle driver. The method comprises steps of:

(a) establishing a personal physiological database comprising steps of:
  periodically sensing the vehicle driver via the physiological sensor to obtain the physiological signals within an initial duration;
  obtaining a mean value and a standard deviation based on the physiological signals; and
  obtaining a tolerance range based on the mean value and the standard deviation, and storing the tolerance range in the personal physiological database;
(b) sensing the vehicle driver via the physiological sensor to obtain at least one instant physiological signal after the initial duration; and
(c) determining whether the at least one instant physiological signal is out of the tolerance range, and outputting an alarm when the at least one instant physiological signal is out of the tolerance range.

The tolerance range stored in the personal physiological database reflects the body status of the vehicle driver before driving the vehicle. When the vehicle driver starts to drive the vehicle, the method of the present invention determines whether the at least one instant physiological signal is out of the tolerance range. When the at least one instant physiological signal is out of the tolerance range, which means that the instant body status is worse than the body status before driving, the method of the present invention would output the alarm to warn the vehicle driver. As a result, before the abnormal body status affects the vehicle driver's action, the alarm outputted by the monitoring device may warn the vehicle driver to stop driving the vehicle and take a rest. The method achieves an effect of early warning to reduce the chance of causing a traffic accident.

On the other hand, the method of the present invention would not use a single constant range for determining different vehicle drivers' physiological signals. The tolerance range stored in the personal physiological database corresponds to the body status of the vehicle driver who will drive the vehicle. For a different vehicle driver, the method of the present invention would generate a different tolerance range for the different vehicle driver. Hence, the determination result in the step (c) of the method of the present invention would precisely reflect the actual body status of the vehicle driver.

DETAILED DESCRIPTION OF THE PREFERRED EMBODIMENT

Figure 1:
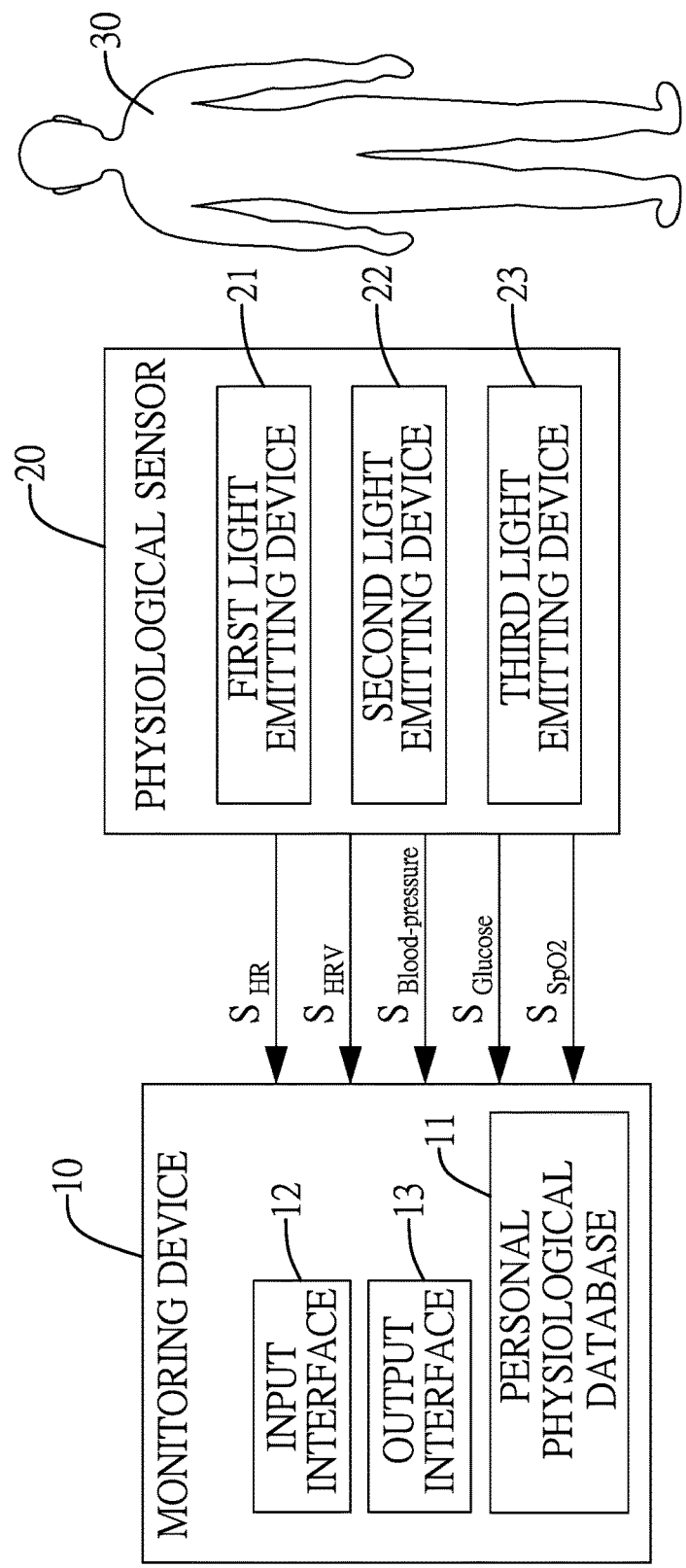
FIG. 1 is a circuit block diagram of a physiological sensor and a monitoring device performing the method of the present invention.

A method for monitoring physiological status of a vehicle driver is disclosed in an embodiment of the present invention. With reference to FIG. 1, the method of the present invention is performed by a monitoring device 10. The monitoring device 10 may be wiredly or wirelessly connected to a physiological sensor 20 for data or control commands transmission. The physiological sensor 20 is adapted to sense a vehicle driver 30 to obtain at least one physiological signal. For example, the monitoring device 10 may be an in-vehicle device or a portable electronic device, such as a smart phone. The monitoring device 10 comprises an input interface 12 and an output interface 13. The input interface 12 may include a touch panel or button(s). The output interface 13 may include a speaker, a display, or a light indicator. The physiological sensor 20 may be mounted on a wearable device, such as a smart Bracelet or a watch.

The physiological sensor 20 may be a conventional Photoplethysmography (PPG) sensor that optically measures the vehicle driver 30's physiological signals. For example, abnormal blood pressure, abnormal blood sugar, or abnormal blood oxygen saturation would affect the heart rate and the heart rate variability of the vehicle driver 30. The heart rate and the heart rate variability are references for estimating the heart attack. In an embodiment, the monitoring device 10 may measure the vehicle driver 30's physiological information including heart rate, heart rate variability, blood pressure, blood sugar, and blood oxygen saturation as indexes for estimating the vehicle driver 30's body status. The physiological sensor 20 comprises multiple light emitting devices for respectively emitting lights in different light wavelengths. For example, the physiological sensor 20 may have a first light emitting device 21, a second light emitting device 22, and a third light emitting device 23. The light emitting devices 21-23 may be light emitting diodes (LED), surface-mount-device (SMD) LEDs, or laser diodes (LD). The first light emitting device 21 emits light in wavelength within 660-740 nanometers (nm), such as 660 nm. The second light emitting device 22 emits light in wavelength within 900-1000 nm, such as 940 nm. The third light emitting device 23 emits light in wavelength within 1000-1800 nm, such as 1550 nm.

A heart rate (HR) signal $S_{HR}$ of the vehicle driver 30 would be measured by only activating the first light emitting device 21. A heart rate variability (HRV) signal $S_{HRV}$ of the vehicle driver 30 would be obtained from a fast-Fourier-transform result of the HR signal $S_{HR}$ by frequency domain analysis. The fast-Fourier-transform and the frequency domain analysis would be performed in the physiological sensor 20 or the monitoring device 10. A blood pressure (BP) signal $S_{Blood-pressure}$ and a blood oxygen saturation (BOS) signal $S_{SpO2}$ of the vehicle driver 30 would be measured by activating the first light emitting device 21 and the second light emitting device 22 at a same time, wherein the BP signal $S_{Blood-pressure}$ is diastolic blood pressure, systolic blood pressure, or both of the diastolic blood pressure and the systolic blood pressure. A blood sugar (BS) signal $S_{Glucose}$ of the vehicle driver 30 would be measured by activating the first light emitting device 21, the second light emitting device 22, and the third light emitting device 23 at a same time.

Hence, as shown in FIG. 1, the physiological signals received by the monitoring device 10 from the physiological sensor 20 may include the HR signal $S_{HR}$, the HRV signal $S_{HRV}$, the BP signal $S_{Blood-pressure}$, the BS signal $S_{Glucose}$, and the BOS signal $S_{SpO2}$.

Figure 2A:
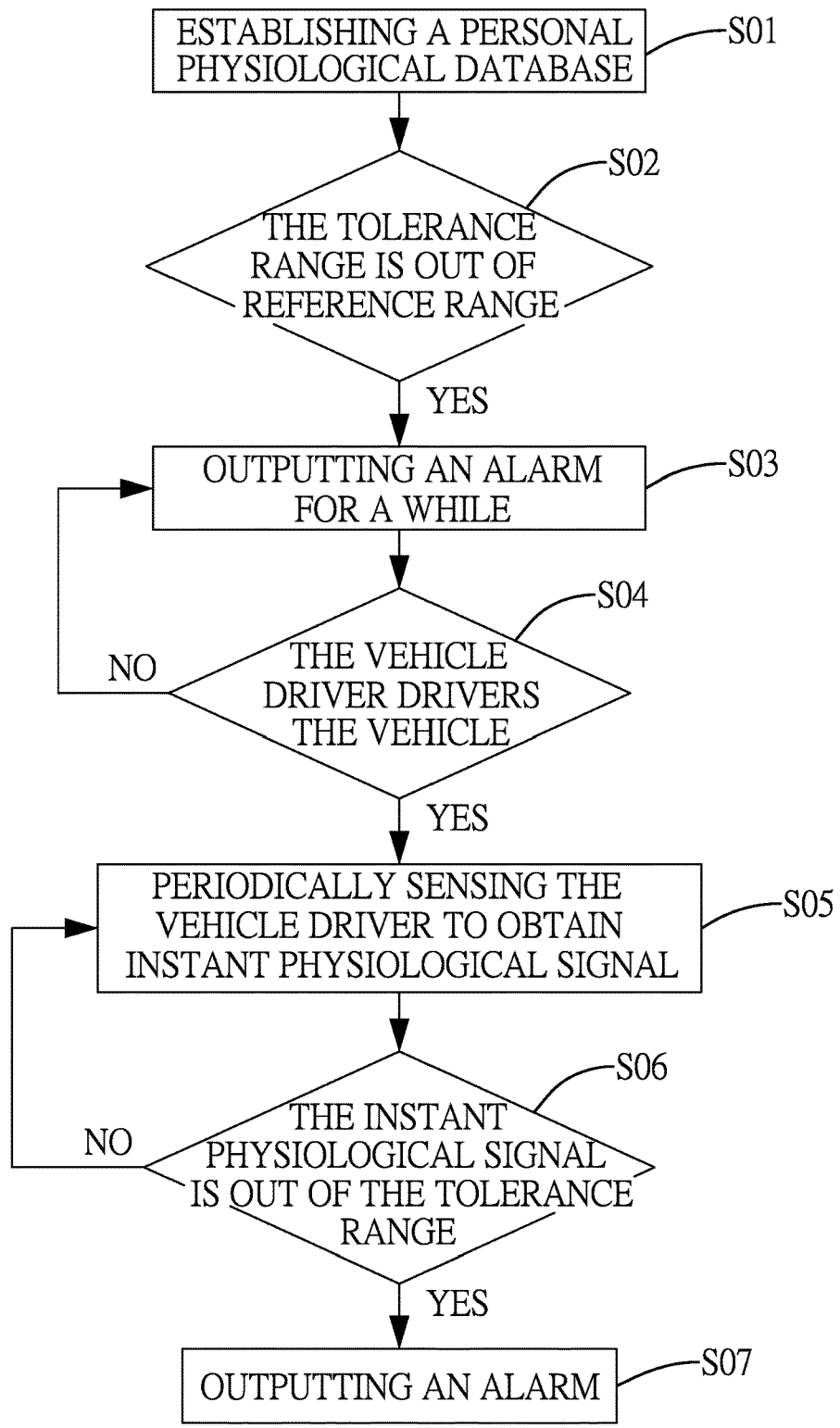
FIGS. 2A, 2B, 2C, and 2D are flow charts of the method of the present invention.
Figure 2B:
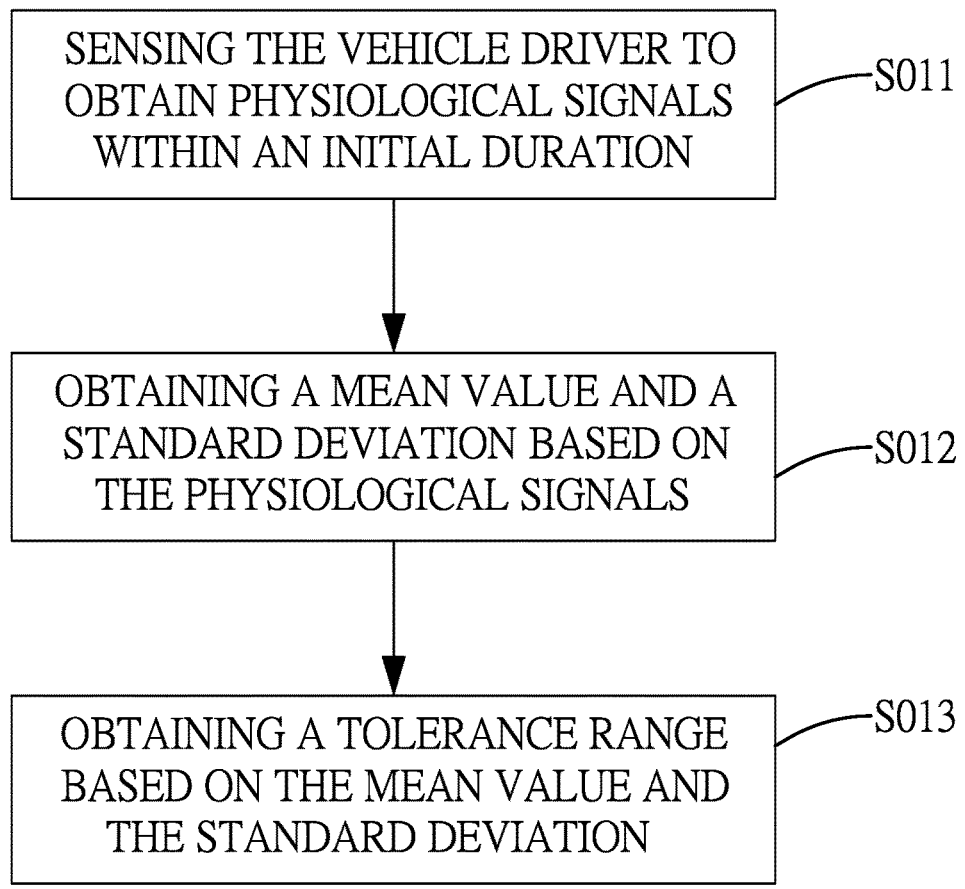

With reference to FIG. 1 and FIG. 2A, an embodiment of the method of the present invention is to establish a personal physiological database 11 (S01) at first. The personal physiological database 11 may be stored in the monitoring device 10. In the step S01, with reference to FIG. 2B, the monitoring device 10 periodically senses the vehicle driver 30 to obtain physiological signals via the physiological sensor 20 within an initial duration (S011). Then, the monitoring device 10 obtains a mean value and a standard deviation based on the physiological signals (S012). Afterwards, the monitoring device 10 obtains a tolerance range based on the mean value and the standard deviation, such that the personal physiological database 11 stores the tolerance range (S013). The tolerance range has a lower boundary and an upper boundary. A summation of the mean value and one time, two times, or three times of the standard deviation is set as the upper boundary of the tolerance range, and a difference between the mean value and one time, two times, or three times of the standard deviation is set as the lower boundary of the tolerance range.

In the step S012, it is to be understood that the mean value is a ratio of a summation of the physiological signals sensed within the initial duration and a number of the physiological signals. The standard deviation may be expressed as below:

$$\sigma = \sqrt{\frac{1}{n-1}\sum_{i=1}^{n}(x_i - \bar{x})^2}$$

where
σ is the standard deviation;
n is the number of the physiological signals sensed within the initial duration;
$x_i$ is an i-th physiological signal of the physiological signals sensed within the initial duration; and
$\bar{x}$ is the mean value of the physiological signals sensed within the initial duration.

Figure 3:
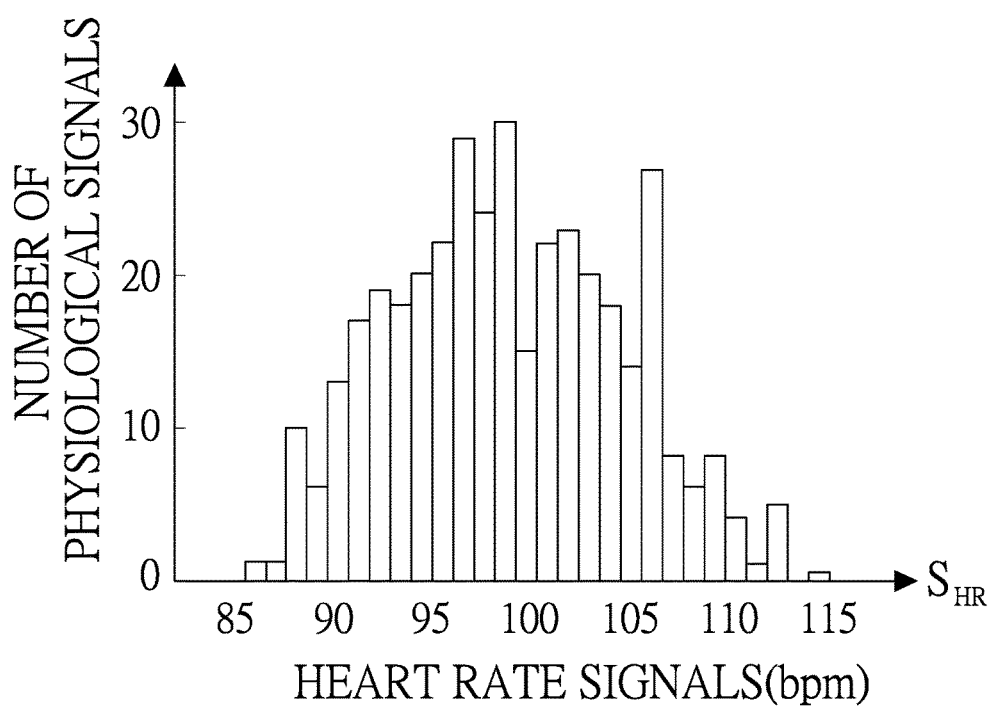
FIG. 3 is a histogram including heart rate signals within the initial duration.
Figure 4:
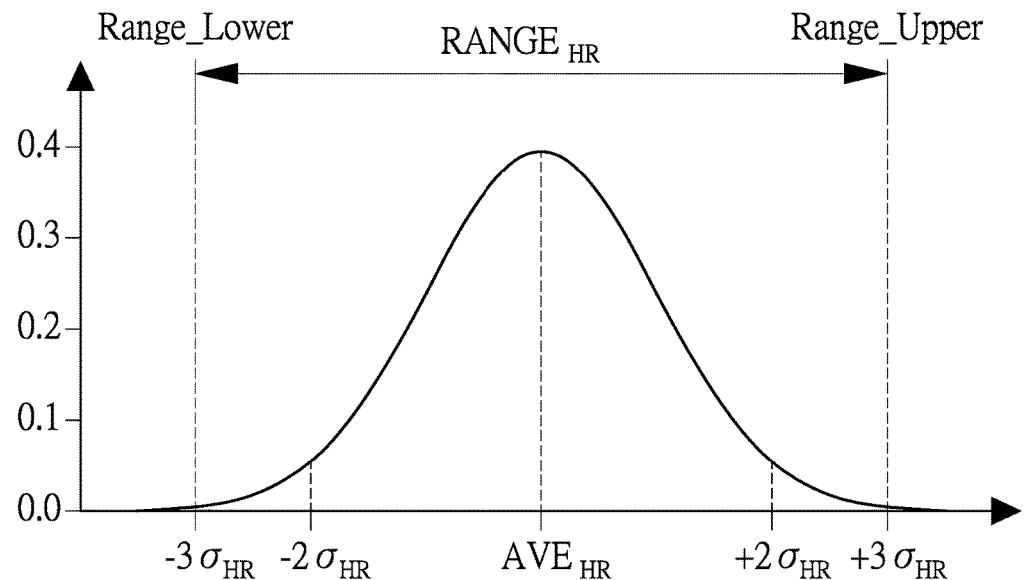
FIG. 4 is a schematic diagram of the heart rate tolerance range $RANGE_{HR}$.

In the embodiment as mentioned above, the monitoring device 10 may receive HR signals $S_{HR}$, HRV signals $S_{HRV}$, BP signals $S_{Blood-pressure}$, BS signals $S_{Glucose}$, and BOS signals $S_{SpO2}$. When the vehicle driver 30 gets in the vehicle, the vehicle driver 30 may turn on the monitoring device 10 and the physiological sensor 20, stays in the vehicle, and does not drive the vehicle for a while, that is, the initial duration, such as 5 minutes. For example, the monitoring device 10 may receive the HR signals $S_{HR}$ within the initial duration as shown in the histogram of FIG. 3. The histogram of FIG. 3 represents a heart rate distribution of the vehicle driver 30 within the initial duration. Then the monitoring device 10 calculates an HR mean value $AVE_{HR}$ and an HR standard deviation $\alpha_{HR}$ based on the HR signals $S_{HR}$ as shown in the normal distribution diagram of FIG. 4. The HR mean value $AVE_{HR}$ calculated from the heart rate distribution in FIG. 3 would be 98.59 beats per minute (bpm) and the HR standard deviation $\sigma_{HR}$ would be 6.6 bpm. After the monitoring device 10 obtains the HR mean value $AVE_{HR}$ and the HR standard deviation $\sigma_{HR}$, the monitoring device 10 calculates an HR tolerance range $RANGE_{HR}$ based on the HR mean value $AVE_{HR}$ and the HR standard deviation $\sigma_{HR}$. The upper boundary Range_upper of the HR tolerance range $RANGE_{HR}$ may be a summation of the HR mean value $AVE_{HR}$ and one time, two times, or three times of the HR standard deviation $\sigma_{HR}$, and the lower boundary Range_lower of the HR tolerance range $RANGE_{HR}$ may be a difference between the HR mean value $AVE_{HR}$ and one time, two times, or three times of the HR standard deviation $\sigma_{HR}$. It is to be deduced that the HR tolerance range $RANGE_{HR}$ calculated from the heart rate distribution in FIG. 3 may be 92-105 bpm, 85-111 bpm, or 79-118 bpm. As the example shown in FIG. 4, the lower boundary Range_lower is the difference between the HR mean value $AVE_{HR}$ and three times of the HR standard deviation $\sigma_{HR}$, and the upper boundary Range_upper is the summation of the HR mean value $AVE_{HR}$ and three times of the HR standard deviation $\sigma_{HR}$.

Figure 5:
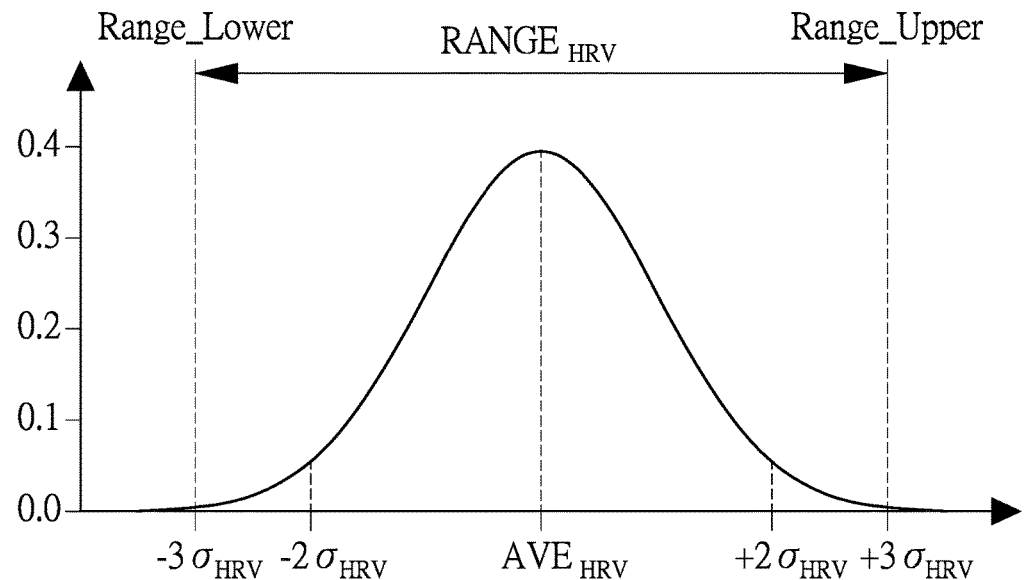
FIG. 5 is a schematic diagram of the heart rate variability tolerance range $RANGE_{HRV}$.
Figure 6:
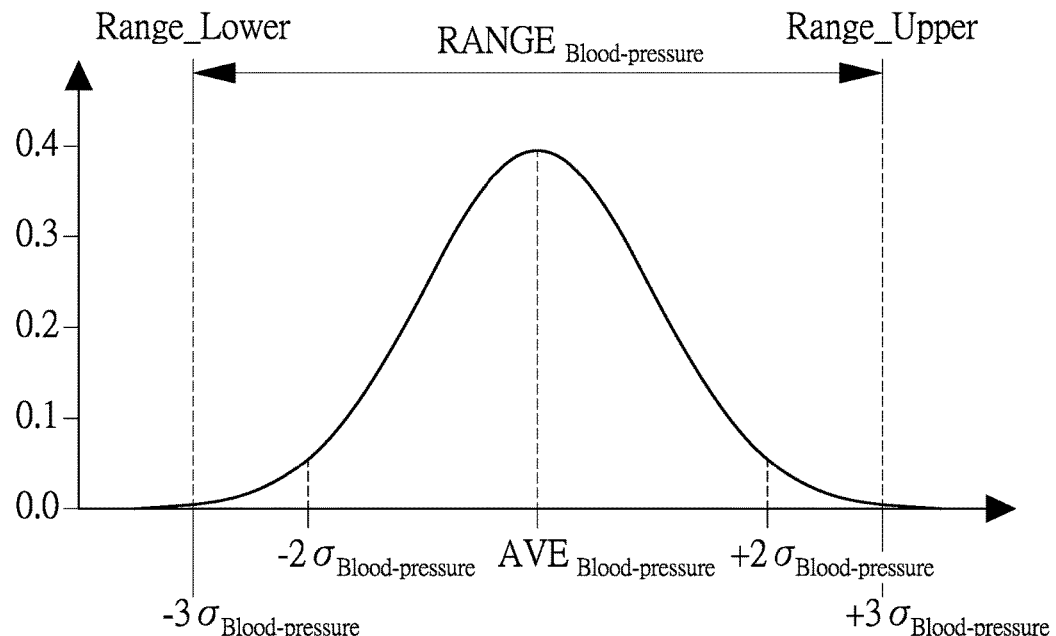
FIG. 6 is a schematic diagram of the blood pressure tolerance range $RANGE_P$.
Figure 7:
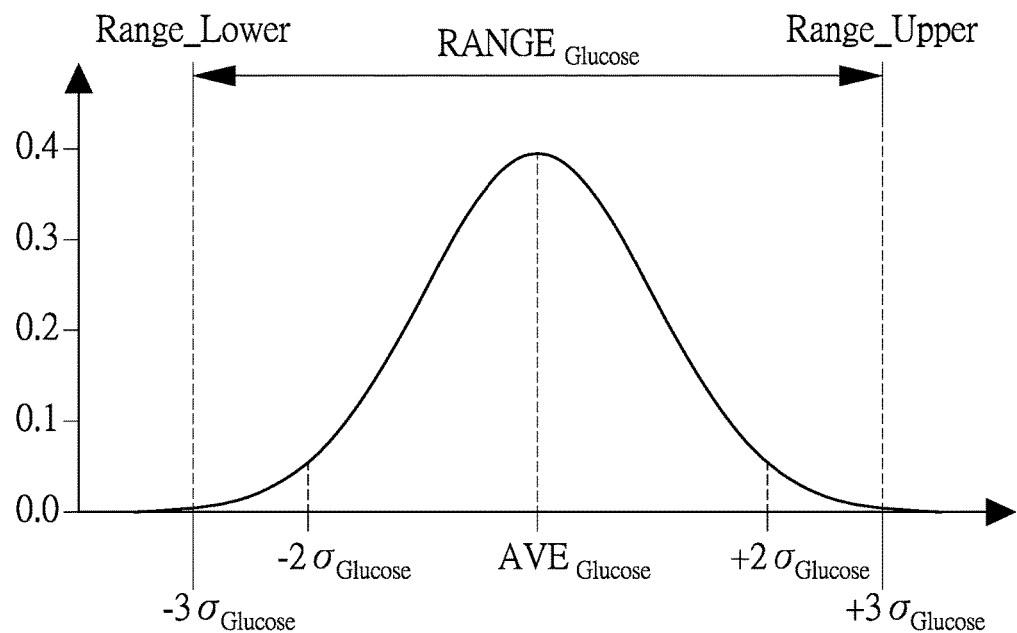
FIG. 7 is a schematic diagram of the blood sugar tolerance range $RANGE_S$.
Figure 8:
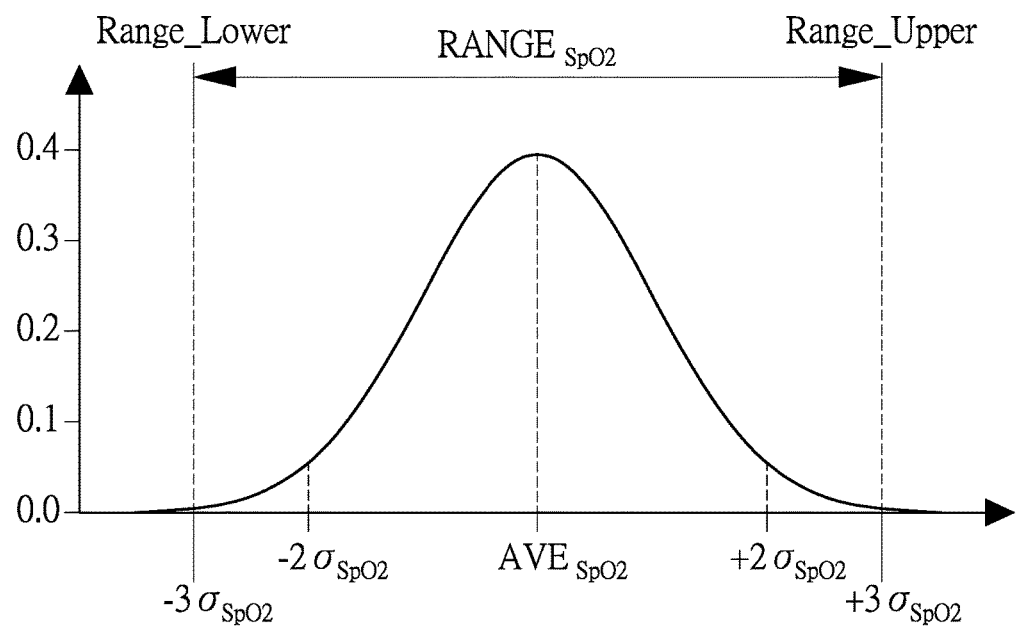
FIG. 8 is a schematic diagram of the blood oxygen saturation tolerance range $RANGE_O$.

HRV tolerance range $RANGE_{HRV}$, BP tolerance range $RANGE_{Blood-pressure}$, BS tolerance range $RANGE_{Glucose}$, and BOS tolerance range $RANGE_{SpO2}$ may be deduced from the HR tolerance range $RANGE_{HR}$. With reference to FIG. 5, the monitoring device 10 calculates an HRV mean value $AVE_{HRV}$ and an HRV standard deviation $\sigma_{HRV}$ based on the HRV signals $S_{HRV}$ and calculates an HRV tolerance range $RANGE_{HRV}$ based on the HRV mean value $AVE_{HRV}$ and the HRV standard deviation $\alpha_{HRV}$. With reference to FIG. 6, the monitoring device 10 calculates a BP mean value $AVE_{Blood-pressure}$ and a BP standard deviation $\sigma_{Blood-pressure}$ based on the BP signals $S_{Blood-pressure}$ and calculates a BP tolerance range $RANGE_{Blood-pressure}$ based on the BP mean value $AVE_{Blood\text{-}pressure}$ and the BP standard deviation $\sigma_{Blood\text{-}pressure}$. With reference to FIG. 7, the monitoring device 10 calculates a BS mean value $AVE_{Glucose}$ and a BS standard deviation $\sigma_{Glucose}$ based on the BS signals $S_{Glucose}$ and calculates a BS tolerance range $RANGE_{Glucose}$ based on the BS mean value $AVE_{Glucose}$ and the BS standard deviation $\sigma_{Glucose}$. With reference to FIG. 8, the monitoring device 10 calculates a BOS mean value $AVE_{SpO2}$ and a BOS standard deviation $\sigma_{SpO2}$ based on the BOS signals $S_{SpO2}$ and calculates a BOS tolerance range $RANGE_{SpO2}$ based on the BOS mean value $AVE_{SpO2}$ and the BOS standard deviation $\sigma_{SpO2}$.

As a result, the tolerance ranges stored in the personal physiological database 11 include the HR tolerance range $RANGE_{HR}$, the HRV tolerance range $RANGE_{HRV}$, the BP tolerance range $RANGE_{Blood\text{-}pressure}$, the BS tolerance range $RANGE_{Glucose}$, and the BOS tolerance range $RANGE_{SpO2}$.

With reference to FIG. 2A, when the personal physiological database 11 is established after the initial duration, the monitoring device 10 determines whether the tolerance range stored in the personal physiological database 11 is out of a reference range (S02). The reference range is stored in the monitoring device 10 and shown in the following table.

| PHYSIOLOGICAL SIGNAL | | REFERENCE RANGE |
| --- | --- | --- |
| HR signal | | 60-100 (bpm) |
| BP signal | diastolic blood pressure | 90-140 (mmHg) |
| | systolic blood pressure | 60-89 (mmHg) |
| BS signal | | 80-120 (mg/dL) |
| BOS signal | | 97-100% |
| HRV signal | | 0.5-2.5 |

When the tolerance range is within the reference range, the vehicle driver 30 may has good physiological status to drive the vehicle and the chance to induce traffic accident is low. When the tolerance range is out of the reference range, the monitoring device 10 controls the output interface 13 to output an alarm (flash lights or sounds) for a while, such as one minutes (S03). Then, the monitoring device 10 question the vehicle driver 30 to determines whether the vehicle driver 30 drivers the vehicle (S04). When the vehicle driver 30 decides not to drive the vehicle, the vehicle driver 30 may control the input interface 12 to send a deny command to the monitoring device 10. When the monitoring device 10 receives the deny command, the monitoring device 10 return to the step S03. When the vehicle driver 30 decides to drive the vehicle, the vehicle driver 30 may control the input interface 12 to send a confirm command to the monitoring device 10.

When the monitoring device 10 receives the confirm command, the monitoring device 10 periodically senses the vehicle driver 30 to obtain at least one instant physiological signal via the physiological sensor 20 (S05). The sensing period may be 5 minutes. In the embodiment, after the initial duration, the vehicle driver 30 may start to drive the vehicle and the monitoring device 10 receives the at least one instant physiological signal of the vehicle driver 30 via the physiological sensor 20. The at least one instant physiological signal includes an instant HR signal, an instant HRV signal, an instant BP signal, an instant BS signal, and an instant BOS signal for reflecting an instant body status of the vehicle driver 30.

After the monitoring device 10 receives the at least one instant physiological signal, the monitoring device 10 determines whether the at least one instant physiological signal is out of the tolerance range (S06). When the instant physiological signal is out of the tolerance range, the monitoring device 10 controls the output interface 13 to output an alarm (S07). In an embodiment, the monitoring device 10 determines whether the instant HR signal is out of the HR tolerance range $RANGE_{HR}$, determines whether the instant HRV signal is out of the HRV tolerance range $RANGE_{HRV}$, determines whether the instant BP signal is out of the BP tolerance range $RANGE_{Blood\text{-}pressure}$, determines whether the instant BS signal is out of the BS tolerance range $RANGE_{Glucose}$, and determines whether the instant BOS signal is out of the BOS tolerance range $RANGE_{SpO2}$. When any one of the instant HR signal, the instant HRV signal, the instant BP signal, the instant BS signal, and the instant BOS signal is out of the corresponding tolerance range, the monitoring device 10 controls the output interface 13 to output the alarm.

Figure 2C:
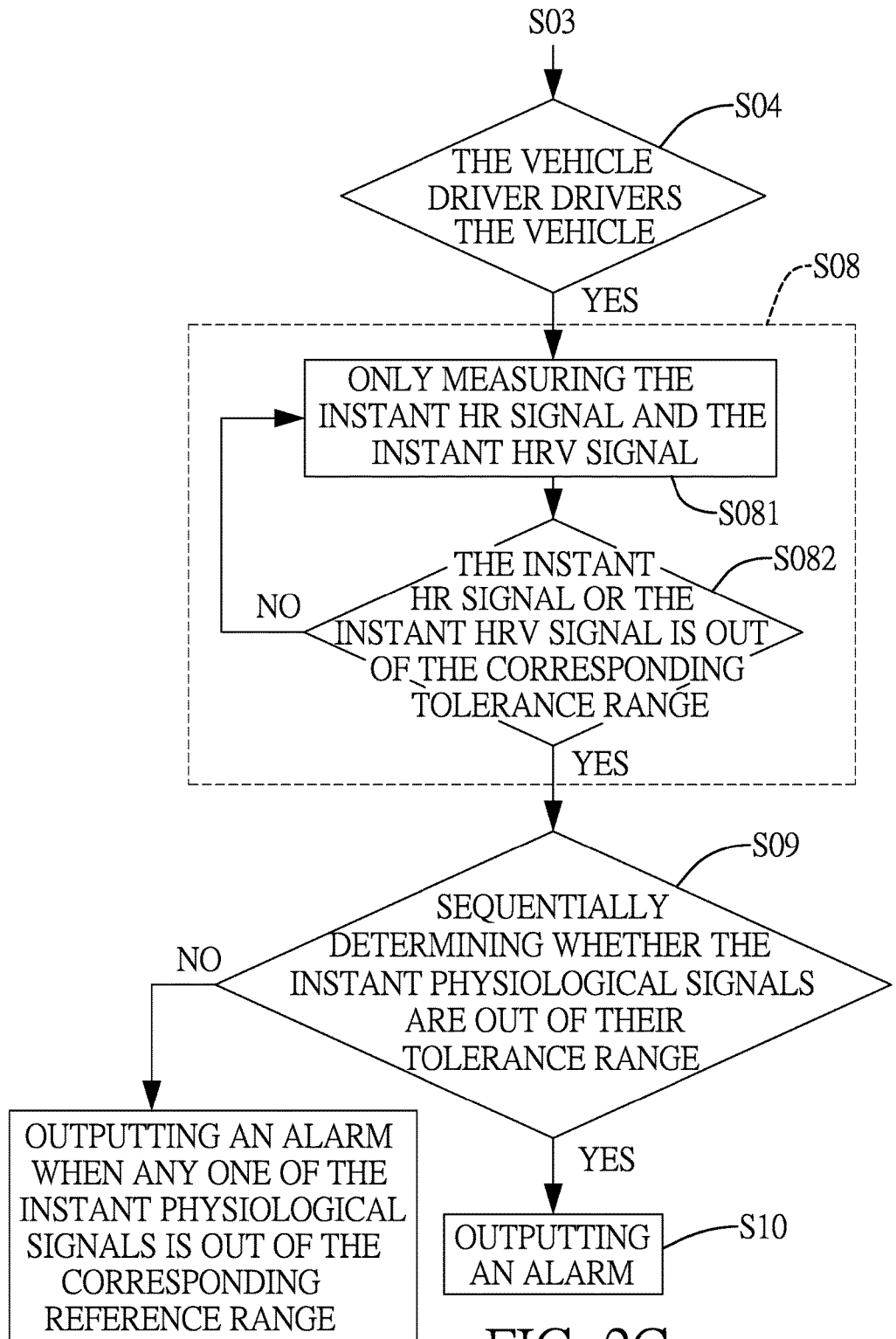

In an embodiment, with reference to FIG. 2C, when the monitoring device 10 receives the confirm command, the monitoring device 10 executes a power-saving mode (S08). When the monitoring device 10 performs the power-saving mode, the monitoring device 10 only measures the instant HR signal and the instant HRV signal (S081) to determine whether the instant HR signal or the instant HRV signal is out of the corresponding tolerance range (S082). When the instant HR signal is out of the HR tolerance range $RANGE_{HR}$ or the instant HRV signal is out of the HRV tolerance range $RANGE_{HRV}$, the monitoring device 10 performs a fast detecting mode to sequentially determine whether the instant BOS signal is out of the BOS tolerance range $RANGE_{SpO2}$, determine whether the instant HR signal is out of the HR tolerance range $RANGE_{HR}$, determines whether the instant HRV signal is out of the HRV tolerance range $RANGE_{HRV}$, determines whether the instant BP signal is out of the BP tolerance range $RANGE_{Blood\text{-}pressure}$, and determines whether the instant BS signal is out of the BS tolerance range $RANGE_{Glucose}$ (S09).

In the step S09, when any one of the instant BOS signal, the instant HR signal, the instant HRV signal, the instant BP signal, and the instant BS signal is out of the corresponding tolerance range, the monitoring device 10 controls the output interface 13 to output the alarm via light flashing or sounds. When all of the instant physiological signals mentioned above are within their tolerance ranges respectively, the monitoring device 10 may determine whether the instant physiological signals are within their reference ranges respectively. When any one of the instant physiological signals is out of the corresponding reference range, the monitoring device 10 controls the output interface 13 to output the alarm.

In the power-saving mode, because the instant HR signal and the instant HRV signal of the vehicle driver 30 would be measured by only activating the first light emitting device 21. The second light emitting device 22 and the third light emitting device 23 are inactivated. As a result, the monitoring device 10 and the physiological sensor 20 may consume less power to achieve the advantage of power-saving.

In the fast detecting mode, the sequence of the instant physiological signals to be determined is based on signal processing speeds. The instant physiological signal with faster signal processing speed would be determined in advance. For example, the processing time for determining whether the instant BOS signal is out of the BOS tolerance range $RANGE_{SpO2}$ would be less than 1 second, the processing time for determining whether the instant HR signal and the HRV signal are out of their tolerance ranges $RANGE_{HR}$, $RANGE_{HRV}$ would be less than 30 seconds, the processing time for determining whether the instant BP signal is out of the BP tolerance range $RANGE_{Blood\text{-}pressure}$ would be less than 150 seconds, and the processing time for determining whether the instant BS signal is out of the BS tolerance range $RANGE_{Glucose}$ would be less than 200 seconds.

Regarding the tolerance range, when the lower boundary/ upper boundary of the tolerance range are the difference/ summation of the mean value and one time or two times of the standard deviation respectively, the tolerance range is narrower to have higher determination sensitivity in the steps S082 and S09. Hence, the monitoring device 10 may sensitively determine the abnormality when the instant physiological signals of the vehicle driver 30 are varied to be out of the narrower tolerance range. In contrast, when the lower boundary/upper boundary of the tolerance range are the difference/summation of the mean value and three times of the standard deviation respectively, the tolerance ranges are wider, such that the instant physiological signals may be varied within the wider tolerance ranges and would not be abnormal. Therefore, the monitoring device 10 in the step S03 would have lower determination sensitivity.

Figure 2D:
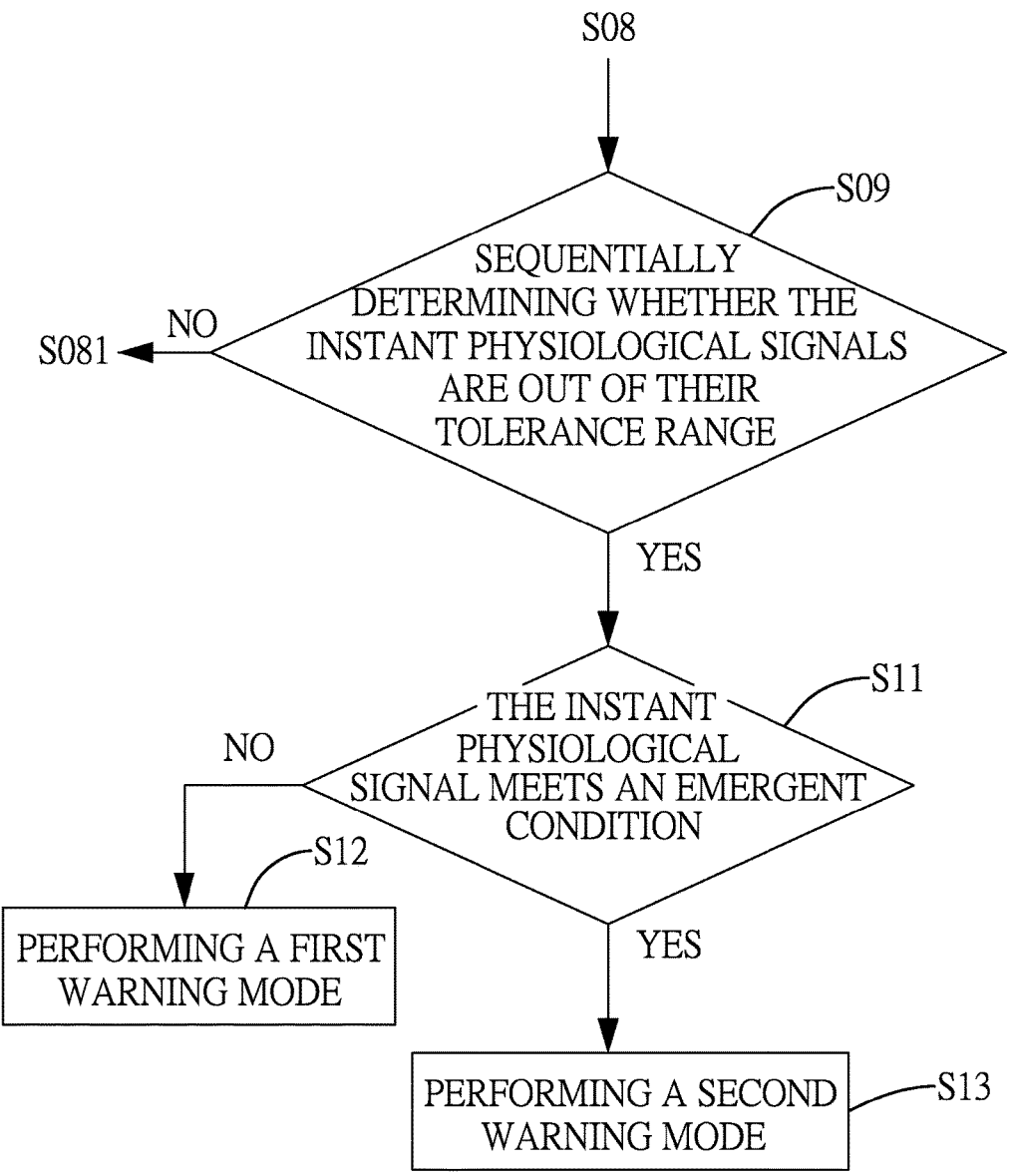
Figure 9:
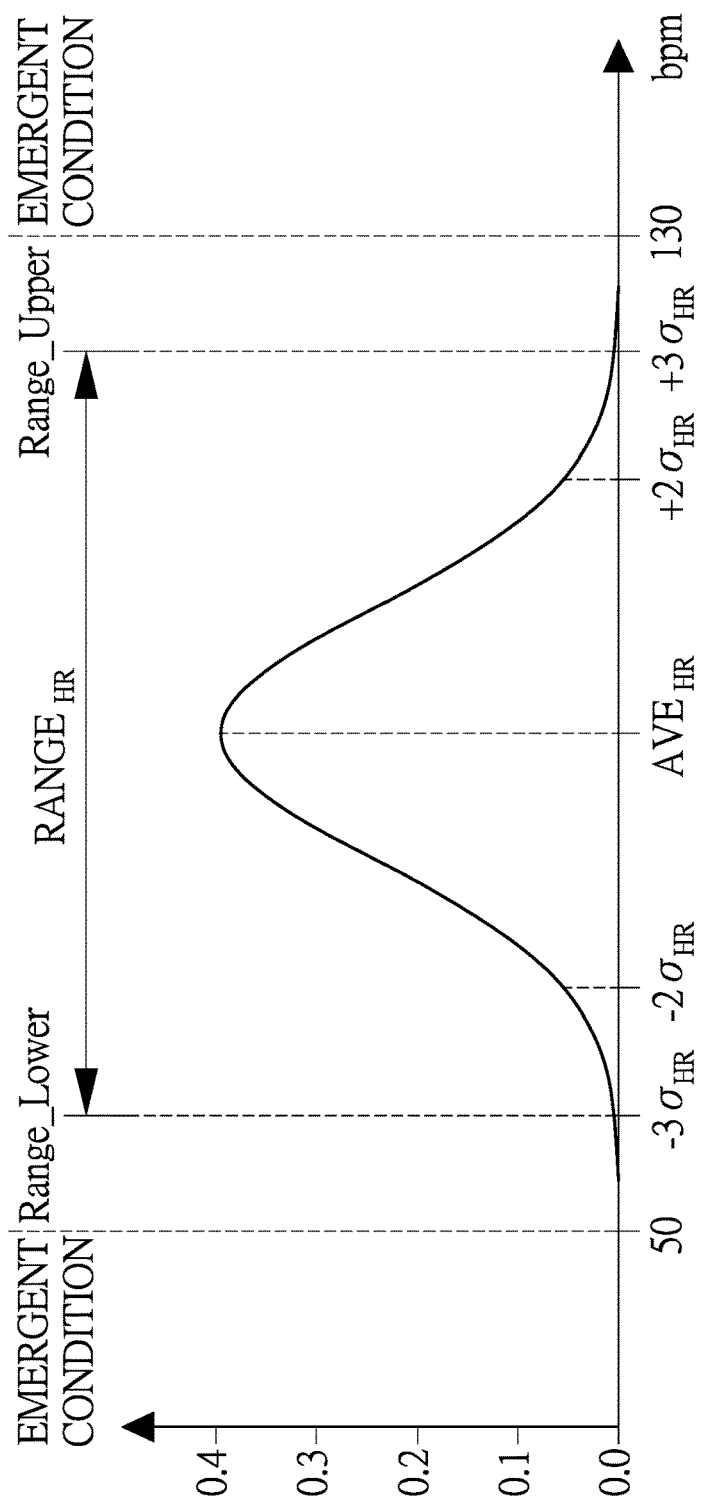
FIG. 9 is a schematic diagram showing the heart rate tolerance range $RANGE_{HR}$ and the emergent conditions.

With reference to FIG. 2D, in another embodiment, when the instant physiological signal is out of the tolerance range in the step S09, the monitoring device 10 further determines whether the instant physiological signal meets an emergent condition (S11). For example, with reference to FIG. 9, the heart rate lower than 50 bpm and higher than 130 bpm may be the emergent condition for the instant HR signal. When the instant physiological signal does not meet the emergent condition, the monitoring device 10 performs a first warning mode to control the output interface 13 to output an alarm via flash lights or sounds (S12). When the instant physiological signal meets the emergent condition, the monitoring device 10 performs a second warning mode to control the output interface 13 to output an alarm via flash lights or sounds (S13). The first warning mode is different from the second warning mode. For example, the first warning mode and the second warning mode are light flashing modes respectively. A light flashing frequency of the second warning mode would be higher than a light flashing frequency of the first warning mode. Therefore, when the physiological signal of the vehicle driver 30 is not only out of the tolerance range but also meets the emergent condition, the monitoring device 10 would output the alarm to warn the vehicle driver 30 to stop driving the vehicle to avoid traffic accident in advance.

In an embodiment, the emergent conditions for the instant HR signal, the instant HRV signal, the instant BP signal, the instant BS signal, and the instant BOS signal are disclosed in the following table.

| INSTANT PHYSIOLOGICAL SIGNAL | | EMERGENT CONDITION |
|---|---|---|
| Instant HR signal | | lower than 50 beats-per-minute or higher than 130 beats-per-minute |
| Instant BP signal | diastolic blood pressure | lower than 89 mmHg or higher than 160 mmHg |
| | systolic blood pressure | lower than 59 mmHg or higher than 100 mmHg |
| Instant BS signal | | lower than 50 mg/dL or higher than 250 mg/dL |
| Instant BOS signal | | lower than 94% |

What is claimed is:

1. A method for monitoring physiological status of a vehicle driver, the method performed by a monitoring device connected to a physiological sensor sensing a vehicle driver to obtain physiological signals of the vehicle driver, wherein the physiological sensor includes a first light-emitting device, a second light-emitting device and a third light-emitting device respectively emitting light in three different light wavelengths and activated for the monitoring device to measure the physiological signals, the method comprising steps of:

(a) establishing a personal physiological database, wherein the step (a) comprises steps of:

periodically sensing the vehicle driver via the physiological sensor to obtain multiple sets of the physiological signals within an initial duration, wherein each set of the physiological signals includes a heart rate (HR) signal, a heart rate variability (HRV) signal, a blood pressure (BP) signal, a blood sugar (BS) signal, and a blood oxygen saturation (BOS) signal, the HR signals in the multiple sets of the physiological signals are measured by only activating the first light-emitting device, the HRV signals in the multiple sets of the physiological signals are obtained from a fast-Fourier-transform result of the HR signals by frequency domain analysis, the BP signals and the BOS signals in the multiple sets of the physiological signals are measured by activating the first light-emitting device and the second light-emitting device simultaneously, and the BS signals in the multiple sets of the physiological signals are measured by activating the first light-emitting device, the second light-emitting device and the third light-emitting device simultaneously;

obtaining multiple mean values and multiple standard deviations corresponding to the respective mean values based on the HR signals, the HRV signals, the BP signals, the BS signals, and the BOS signals in the multiple sets of the physiological signals respectively; and obtaining a tolerance range based on each mean value and a corresponding standard deviation, and storing the tolerance ranges in the personal physiological database, wherein the tolerance ranges stored in the personal physiological database includes an HR tolerance range, an HRV tolerance range, a BP tolerance range, a BS tolerance range, and a BOS tolerance range, and each of the HR tolerance range, the HRV tolerance range, the BP tolerance range, the BS tolerance range, and the BOS tolerance range has a lower boundary and an upper boundary;

(b) sensing the vehicle driver via the physiological sensor to obtain an instant HR signal and an instant HRV signal after the initial duration; and (c) determining whether in a power-saving mode any one of a condition that the instant HR signal is out of the HR tolerance range and a condition that the instant HRV signal is out of the HRV tolerance range is met;

(d) obtaining an instant set of the physiological signals to sequentially determine whether the BOS signal, the HR signal, the HRV signal, the BP signal, the BS signal of the instant set of the physiological signals are respectively out of the BOS tolerance range, the HR tolerance range, the HRV tolerance range, the BP tolerance range, and the BS tolerance range in a fast detecting mode when in the power-saving mode any one of the condition that the instant HR signal is out of the HR tolerance range and the condition that the instant HRV signal is out of the HRV tolerance range is met, wherein a sequence of the BOS signal, the HR signal, the HRV signal, the BP signal, the BS signal of the instant set of the physiological signals to be determined in the fast detecting mode is arranged in a descending order of a signal processing speed in determining whether each of the BOS signal, the HR signal, the HRV signal, the BP signal, the BS signal of the instant set of the physiological signals is out of a corresponding one of the BOS tolerance range, the HR tolerance range, the HRV tolerance range, the BP tolerance range, and the BS tolerance range;
(e) outputting an alarm when any one of the BOS signal, the HR signal, the HRV signal, the BP signal, and the BS signal of the instant set of the physiological signals is out of a corresponding one of the BOS tolerance range, the HR tolerance range, the HRV tolerance range, and the BP tolerance range, and the BS tolerance range in the fast detecting mode.

2. The method as claimed in claim 1 further comprising:
determining whether the instant set of the physiological signals meets an emergency condition when when any one of the BOS signal, the HR signal, the HRV signal, the BP signal, and the BS signal of the instant set of the physiological signals is out of the corresponding one of the BOS tolerance range, the HR tolerance range, the HRV tolerance range, and the BP tolerance range, and the BS tolerance range in the fast detecting mode in the step (d), wherein the emergency condition means that any one of the BOS signal, the HR signal, the HRV signal, the BP signal, and the BS signal of the instant set of the physiological signals is out of a reference range with at least one of an upper bound and a lower bound respectively greater than and less than the upper boundary and the lower boundary of the corresponding one of the BOS tolerance range, the HR tolerance range, the HRV tolerance range, and the BP tolerance range, and the BS tolerance range;
performing a first warning mode when the instant set of the physiological signals does not meet the emergency condition; and
performing a second warning mode when the instant set of the physiological signals meets the emergency condition, wherein the first warning mode is different from the second warning mode.

3. The method as claimed in claim 2, wherein the at least one of the lower bounds and the higher bounds of the reference ranges includes:
a heart rate lower than 50 beats per minute and a heart rate higher than 130 beats per minute corresponding to the HR signal;
a diastolic blood pressure lower than 89 mmHg and a diastolic blood pressure higher than 160 mmHg corresponding to the BP signal;
a systolic blood pressure lower than 59 mmHg and a systolic blood pressure higher than 100 mmHg corresponding to the BP signal;
a blood sugar lower than 50 mg/dL and a blood sugar higher than 250 mg/dL corresponding to the BS signal; and
a blood oxygen saturation lower than 94%.

4. The method as claimed in claim 2, wherein the first warning mode and the second warning mode are light flashing modes respectively;
a light flashing frequency of the second warning mode is higher than a light flashing frequency of the first warning mode.

5. The method as claimed in claim 3, wherein the first warning mode and the second warning mode are light flashing modes respectively;
a light flashing frequency of the second warning mode is higher than a light flashing frequency of the first warning mode.

6. The method as claimed in claim 1, wherein in the step (a), a summation of each mean value and two times of a corresponding standard deviation is set as an upper boundary of a corresponding one of the HR tolerance range, the HRV tolerance range, the BP tolerance range, the BS tolerance range, and the BOS tolerance range, and a difference between the mean value and two times of the corresponding standard deviation is set as a lower boundary of the corresponding one of the HR tolerance range, the HRV tolerance range, the BP tolerance range, the BS tolerance range, and the BOS tolerance range.

7. The method as claimed in claim 2, wherein in the step (a), a summation of each mean value and two times of a corresponding standard deviation is set as an upper boundary of a corresponding one of the HR tolerance range, the HRV tolerance range, the BP tolerance range, the BS tolerance range, and the BOS tolerance range, and a difference between the mean value and two times of the corresponding standard deviation is set as a lower boundary of the corresponding one of the HR tolerance range, the HRV tolerance range, the BP tolerance range, the BS tolerance range, and the BOS tolerance range.

8. The method as claimed in claim 3, wherein in the step (a), a summation of each mean value and two times of a corresponding standard deviation is set as an upper boundary of a corresponding one of the HR tolerance range, the HRV tolerance range, the BP tolerance range, the BS tolerance range, and the BOS tolerance range, and a difference between the mean value and two times of the corresponding standard deviation is set as a lower boundary of the corresponding one of the HR tolerance range, the HRV tolerance range, the BP tolerance range, the BS tolerance range, and the BOS tolerance range.

9. The method as claimed in claim 1, wherein in the step (a), a summation of each mean value and three times of a corresponding standard deviation is set as an upper boundary of a corresponding one of the HR tolerance range, the HRV tolerance range, the BP tolerance range, the BS tolerance range, and the BOS tolerance range, and a difference between the mean value and three times of the corresponding standard deviation is set as a lower boundary of the corresponding one of the HR tolerance range, the HRV tolerance range, the BP tolerance range, the BS tolerance range, and the BOS tolerance range.

10. The method as claimed in claim 2, wherein in the step (a), a summation of each mean value and three times of a corresponding standard deviation is set as an upper boundary of a corresponding one of the HR tolerance range, the HRV tolerance range, the BP tolerance range, the BS tolerance range, and the BOS tolerance range, and a difference between the mean value and three times of the corresponding standard deviation is set as a lower boundary of the corresponding one of the HR tolerance range, the HRV tolerance range, the BP tolerance range, the BS tolerance range, and the BOS tolerance range.

11. The method as claimed in claim 3, wherein in the step (a), a summation of each mean value and three times of a corresponding standard deviation is set as an upper boundary of a corresponding one of the HR tolerance range, the HRV tolerance range, the BP tolerance range, the BS tolerance range, and the BOS tolerance range, and a difference between the mean value and three times of the corresponding standard deviation is set as a lower boundary of the corresponding one of the HR tolerance range, the HRV tolerance range, the BP tolerance range, the BS tolerance range, and the BOS tolerance range.

* * * * *